United States Patent [19]

Michel

[11] Patent Number: 4,517,963
[45] Date of Patent: May 21, 1985

[54] IMAGE-ERECTING BARREL ROTATOR FOR ARTICULATED OPTICAL ARM

[75] Inventor: Thomas J. Michel, Miami, Fla.
[73] Assignee: Harold Unger, Miami Beach, Fla.
[21] Appl. No.: 455,575
[22] Filed: Jan. 4, 1983
[51] Int. Cl.³ .............................................. A61B 1/06
[52] U.S. Cl. ....................................... 128/6; 351/211
[58] Field of Search ...................................... 128/4–8, 128/303.1, 56; 351/211; 414/910

[56] References Cited

U.S. PATENT DOCUMENTS

| | | | |
|---|---|---|---|
| 3,994,557 | 11/1976 | Hopkins | 128/4 |
| 4,122,853 | 10/1978 | Smith | 128/303.1 |
| 4,266,862 | 5/1981 | Trotscher et al. | 351/211 |
| 4,277,168 | 7/1981 | Oku | 128/4 |
| 4,407,272 | 10/1983 | Yamaguchi | 128/6 |

Primary Examiner—Edward M. Coven
Assistant Examiner—Max F. Hindenburg
Attorney, Agent, or Firm—Michael Ebert

[57] ABSTRACT

An articulated optical arm adapted to optically link an endoscopic telescope to a viewing station through a series of mechanically interhinged and optically intercoupled arm sections, the last arm in the series being coupled to a terminal eyepiece through an image-erecting barrel which is rotatable by a barrel rotator to correct for image displacement. Associated with the endoscope are surgical instruments for performing an operation at the surgical site viewed by the endoscope. In order to make it possible for a surgeon while manipulating the instrument with his hands to rotate the barrel to maintain an erect image, the barrel rotator includes a bi-directional motor controlled by a foot-operated switch. When foot-actuated in one way, the switch causes the motor to turn the barrel clockwise; and when foot-actuated in another way, it causes the motor to turn the barrel counterclockwise whereby the surgeon is able to maintain proper image orientation throughout a procedure in the course of which the articulated arm undergoes adjustment that acts to displace the image.

9 Claims, 5 Drawing Figures

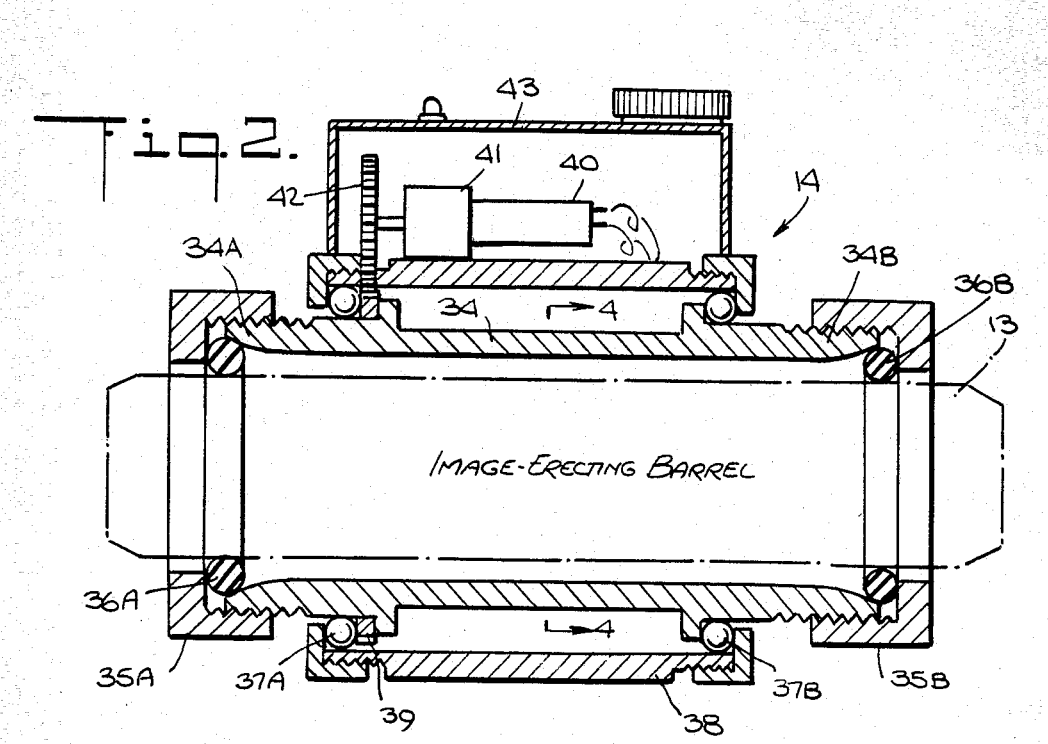
Fig. 2.
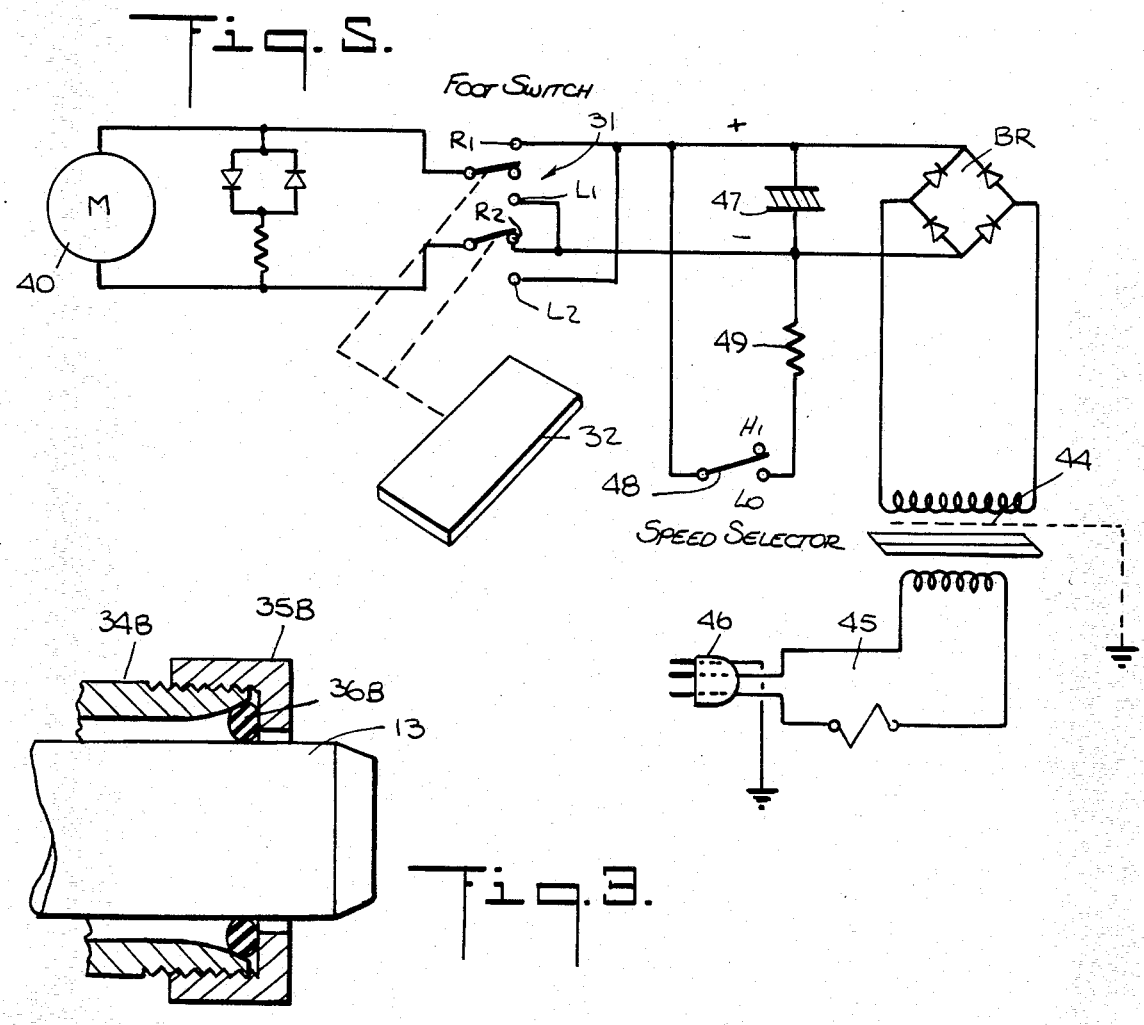
Fig. 5.
Fig. 3.

4,517,963

IMAGE-ERECTING BARREL ROTATOR FOR ARTICULATED OPTICAL ARM

BACKGROUND OF INVENTION

Field of Invention

This invention relates generally to endoscopic instrumentation, and more particularly to an articulated optical arm adapted to optically link an endoscopic telescope to a viewing station through an image-erecting optical barrel which is rotatable by a remotely-controlled barrel rotator whereby the image being viewed may be properly oriented.

An endoscope is an instrument for visualizing the interior of a hollow organ such as the rectum or urethra. A typical modern endoscope for surgical procedures includes a tubular cannula that is insertable into a body cavity, the cannula incorporating imaging means leading to a telescope, making it possible to directly view the region of interest through the eyepiece of the telescope.

The endoscopic telescope is provided with an adapter to which is attachable a flexible fiber optic cable coupled to a light source, thereby illuminating the region being observed. Also, a raceway or other means to accommodate scalpels, forceps and other surgical tools expressly designed to function within a stainless steel tube forming the external sheath of the endoscope can be included.

Normally, when observing an internal site through the endoscopic telescope, the viewer brings his eye close to the eyepiece. But when performing surgery, one cannot look into the eyepiece without having the face of the viewer interfere with the fingers manipulating the surgical instrument, for the instrument handles are in the proximity of the eyepiece.

One function of an articulated optical arm is to make it possible for a surgeon to view an internal organ through an endoscopic telescope from a viewing station well separated from the telescope, so that the surgeon is able, without difficulty, to manipulate the surgical instruments associated with the endoscope. Typical of commercially-available articulated optical arms is the model 29023 device manufactured by Karl Storz Gmbh & Co. of West Germany. This device fits all endoscopic telescopes and serves to optically link the telescope to a film or video camera while permitting simultaneous observation by the operator and an observer.

An articulated optical arm is composed of a series of arm sections which are mechanically interhinged and optically intercoupled by special joints. Each section houses a solid quartz rod to transmit the image, and each joint includes a pair of optically-coupled prisms to transfer the image from one arm section to the next, regardless of the relative angular positions thereof.

The first section in the series is coupled to the endoscopic telescope; and by adjusting the sections of the articulated arm relative to each other, one can extend, retract or otherwise shift the position of the endoscope in the body cavity while maintaining an uninterrupted optical link between the endoscope and the viewing station. However, as such adjustments are made, the relative orientation of the image transfer prisms in each joint is altered, with a consequent rotation of the image about the optical axis.

It is for this reason that the last in the series of sections is coupled to the terminal eyepiece of the articulated arm through a rotatable barrel which houses an image-erecting prism. By manually rotating this barrel clockwise or counterclockwise, the observer is able to restore the image to its proper orientation, regardless of the degree and direction of image displacement resulting from a given arm adjustment.

When the terminal eyepiece of the articulated arm is coupled to the video camera of a TV monitor, a surgeon is then able to advantageously view the surgical site as a magnified illuminated display on a TV screen rather than through the limited confines of an eyepiece. The articulated arm may include at its terminal, a beam splitter which divides the image between a lens coupling the arm to a video camera (or a recording motion picture camera) and an auxiliary eyepiece, so that one may simultaneously observe and record the surgical site in the course of an endoscopic procedure.

The term "viewing station" as used herein encompasses whatever arrangement is provided in conjunction with the terminal eyepiece of the articulated arm to examine and/or record the body region visualized through the endoscope associated with the arm.

The problem to which the present invention is addressed is the practical difficulty experienced by an operating surgeon with conventional articulated arms during an endoscopic procedure. The surgeon's hands are engaged in manipulating the surgical instruments, yet he is also called upon from time to time to shift the position of the endoscope so that he can properly view various aspects of the region in which he is operating. In making these shifts, the articulated arm is adjusted accordingly. But with each new adjustment of the articulated arm, the image transmitted through the arm undergoes circumferential displacement about the optical axis in a direction and to a degree that depends on the nature of the adjustment.

It becomes necessary, therefore, with each adjustment which may occur with a fair degree of frequency in the course of the procedure, for the surgeon to rotate the barrel in order to re-erect the image presented at the viewing station. But the surgeon has only two hands, and if these are occupied in manipulating the instruments, he may either have to interrupt the procedure to turn the barrel, or he may be forced to make an accommodation to the displaced image.

Thus if at a critical juncture, the surgeon is faced with an upside-down image of the internal region being operated on, and he is then not in a position to rotate the image-erecting barrel, he must then take the inverted image into account when manipulating his instruments. This gives rise to serious eye-to-hand or psychomotor coordination difficulties and may further complicate an already complicated procedure.

Another factor which comes into play is the maintenance of sterility. Surgical instruments must be cleaned and sterilized prior to use, and the surgeon takes steps before a procedure to disinfect his hands and to put on sterile gloves. But articulated optical arms cannot be disinfected or sterilized; hence if the surgeon manipulates the image-erecting barrel with his hands, he may thereby violate the field of sterility.

SUMMARY OF INVENTION

In view of the foregoing, the main object of this invention is to provide a barrel rotator adapted to engage the image-erecting barrel of an articulated optical arm which optically links an endoscopic telescope to a viewing station, the rotator making it possible to control barrel rotation from a remote control station, thereby obviating the need to manually rotate the barrel.

More particularly, an object of this invention is to provide an image-erecting barrel rotator of the above type which includes a sleeve into which is telescoped the image-erecting barrel, the barrel being clamped within the sleeve which is turnable in either direction by a bi-directional motor whose operation is controlled from the remote control station.

Also an object of the invention is to provide a barrel rotator of the above type having a pedal-operated switching mechanism at the remote station which may be actuated by the surgeon's foot, so that the surgeon's hands which manipulate sterilized surgical instruments are never used to turn the barrel; hence the field of sterility is never violated.

A significant advantage of the present invention is that it makes it possible in an endoscopic procedure for the operating surgeon to see a magnified illuminated image display of the operating site on the screen of a TV monitor while his hands manipulate the surgical instruments, and with his foot to re-erect the displayed image whenever the articulated arm which optically couples the endoscopic telescope to the video camera of the monitor is adjusted. Because the shoes of the surgeon are outside the field of sterility, this field is not violated by the barrel rotator.

Yet another object of the invention is to provide a barrel rotator which operates efficiently and reliably, and which may be manufactured at relatively low cost.

Briefly stated, a barrel rotator in accordance with the invention comprises a primary assembly that includes a sleeve adapted to receive and clamp onto the image-erecting barrel of an articulated optical arm which optically links an endoscopic telescope to a viewing station, the sleeve being mechanically coupled to a bi-directional motor which is connected by a cable to a remote control station.

In a preferred embodiment, the motor is controlled from a control station by a foot pedal switching mechanism which when rocked by the foot of the operator to one side, acts to connect a dc power supply to the motor in a polarity causing the motor to turn the barrel in the clockwise direction; and when rocked to the opposite side, applies the power in the reverse polarity to cause the motor to turn the barrel in the counterclockwise direction. Thus a surgeon while his hands are engaged is able with his foot to rotate the image presented at the viewing station in a direction and to a degree sufficient to correct for image displacement resulting from adjustment of the articulated arm.

OUTLINE OF DRAWINGS

For a better understanding of the invention as well as other objects and further features thereof, reference is made to the following detailed description to be read in conjunction with the accompanying drawings, wherein:

FIG. 2 is a sectional view of the primary assembly of the barrel rotator;

FIG. 3 illustrates the manner in which the sleeve of the barrel rotator clamps onto the image-erecting barrel;

FIG. 4 is a transverse section taken in the plane indicated by line 4—4 in FIG. 2; and FIG. 5 is a schematic diagram of the power supply and the switching mechanism for controlling the motor of the barrel rotator.

DESCRIPTION OF INVENTION

The Basic System

Figure 1:
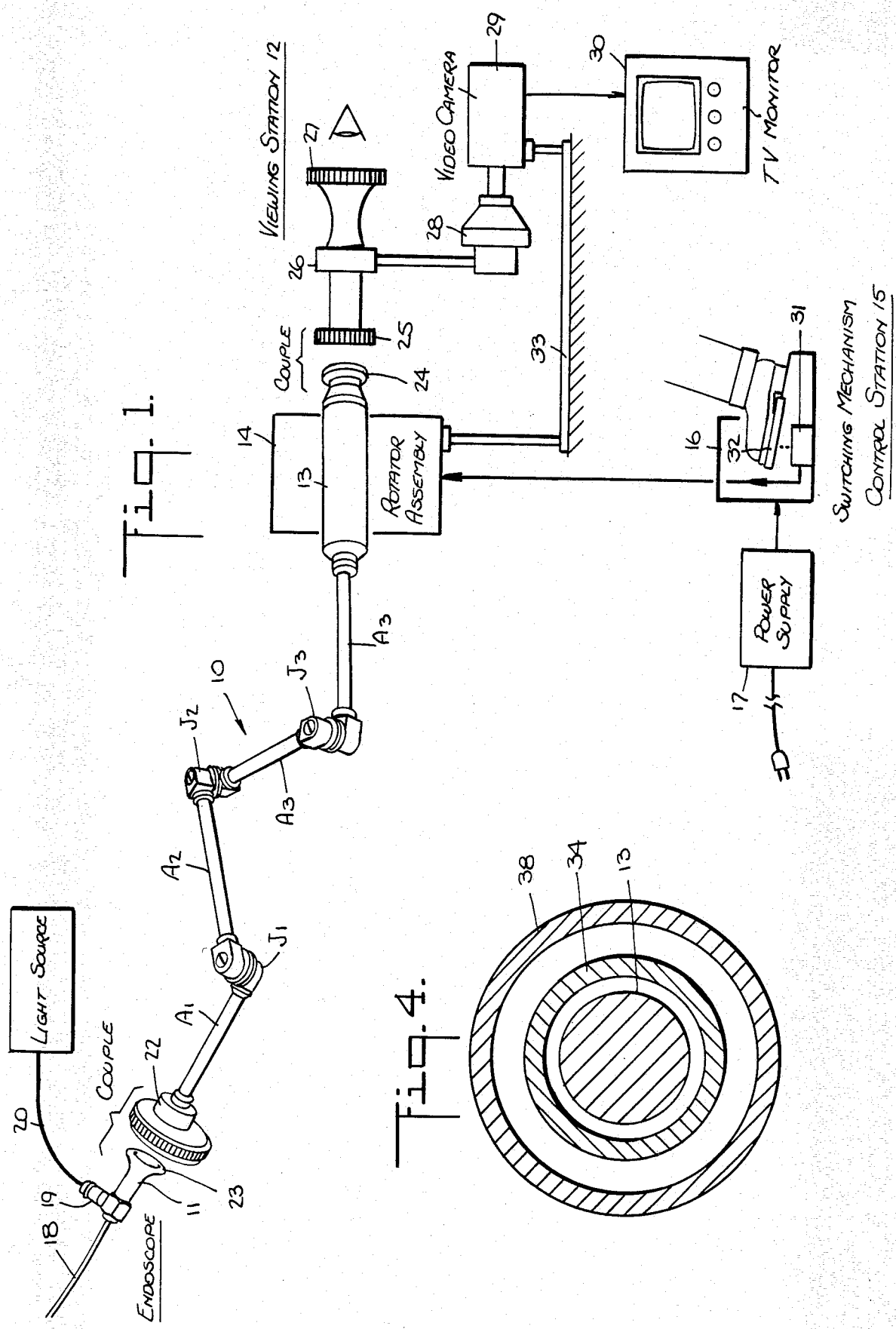
FIG. 1 illustrates an articulated optical arm which optically links an endoscopic telescope to a viewing station, the image-erecting barrel of the arm being rotated by a barrel rotator in accordance with the invention.

Referring now to FIG. 1, there is shown an articulated optical arm, generally designated by numeral 10, for optically linking an endoscopic telescope 11 to a viewing station 12, the rotatable image-erecting barrel 13 of the arm being telescoped and clamped within the sleeve of a primary assembly 14 of a barrel rotator in accordance with the invention, rotation of the sleeve being remotely controlled from a control station 15 provided with a foot-operated mechanism 16 and a power supply 17.

Telescope 11 is mounted at the end of a conventional endoscope 18 which is insertable into a body cavity for visualizing an interior region of medical interest. Associated with the endoscope are surgical tools (not shown) for carrying out a surgical procedure at the site being viewed. The telescope is provided with a lateral adapter 19 to which a fiber optic cable 20 is coupled to conduct light from a suitable light source 21 to illuminate the region being viewed.

The articulated arm 10, illustrated in FIG. 1, is composed of a series of three arm sections $A_1$, $A_2$ and $A_3$ which are mechanically interhinged and optically intercoupled by special joints $J_1$, $J_2$ and $J_3$. Each arm section houses a solid quartz image-transmitting rod, and each joint includes a pair of optically-coupled prisms to transfer the image from one arm section to the next regardless of the relative angular positions thereof.

While only three arm sections are shown, in practice a greater number may be included in the articulated optical arm. As pointed out previously, adjustment of the arm causes the prisms in the joints to change their relative orientation and results in rotation of the image. The invention is usable with any commercially-available articulated optical arm.

The first arm section $A_1$ is provided at its free end with an optical coupler 22 which fits onto eyepiece 23 of the endoscopic telescope 11. The last arm section $A_3$ is connected to rotatable barrel 13 which houses an image-erecting prism and which is provided with a terminal eyepiece 24 so that the image seen through this eyepiece which is caused to rotate as the arm is adjusted, may be re-erected by rotation of the barrel in the direction and to the extent appropriate to a given arm adjustment.

Because of the articulated arm, the operator is able to extend, retract or otherwise shift the endoscope within the body cavity so that any aspect of the internal region may be clearly visualized at the viewing station without the need to bring the eye of the viewer into the immediate proximity of the telescope eyepiece 23. As a consequence, when the endoscope is provided with surgical tools, there is no interference between the hands of the surgeon manipulating these tools and his face, for his face is at the viewing station 12 well separated from the telescope.

At viewing station 12, an optical coupler 25 is provided which fits onto terminal eyepiece 24 of the articulated arm 10. Optical coupler 25 is secured to a beam splitter 26 which is arranged to convey the image of the region being viewed both to a conventional auxiliary eyepiece 27 and to the input lens assembly 28 of a video camera 29 included in a closed circuit, high-resolution TV system provided with a TV monitor 30.

An operating surgeon may therefore view the region of interest through auxiliary eyepiece 27 or in a magnified display on the screen of TV monitor 30. The invention is not limited to the viewing station arrangement shown. Thus the surgeon may operate while viewing the region of interest on the TV screen, and a motion picture camera may be coupled to auxiliary eyepiece 27 to record this operation.

Primary assembly 14 is provided with a bi-directional dc motor to which power is supplied from power supply 17 through the pedal-operated switching mechanism 16. In this way, an operating surgeon, while viewing the operating site through the articulated optical arm and while manipulating surgical tools with his hands, may at the same time with his foot act to control the rotation of the image-erecting barrel so as to re-erect the image each time an arm adjustment is made which displaces the displayed image.

The switching mechanism 16 activated by the foot of the surgeon comprises a switch 31 operatively coupled to a foot pedal 32 which is pivotally mounted so that it can be rocked about a central axis by the foot which engages the pedal from one side to the opposite side. The relationship of switch 31 to dc power supply 17 and the motor of the primary assembly is such that when the pedal is rocked to the right, the switch then applies power to the motor in a polarity causing it to turn the image-erecting barrel in the clockwise direction, this polarity being reversed when the pedal is rocked to the left to cause turning in the counterclockwise direction.

Thus the operating arrangement is compatible with human engineering requirements and lends itself to simple psychomotor coordination. When an arm adjustment results in image rotation displaced from the erect state in the counterclockwise direction, the operator then rocks the foot pedal toward the right and watches the displayed image as it is caused to rotate clockwise, the foot being released from the pedal when the image assumes its proper erect orientation, this release causing the switch to assume its neutral or "off" position. And when an arm adjustment gives rise to image rotation displaced from the erect state in the clockwise direction, the operator then rocks the foot pedal toward the left to effect a corrective counterclockwise rotation.

Primary assembly 14 and video camera 29 are mounted on the arms of a stationary bracket 33 so that they occupy a fixed stable position, only the sections of the articulated arm and the associated endoscope being adjustably positioned. The bracket may be mounted on a camera tripod so that the entire system may be conveniently set up in an operating room. In practice, the power supply may be integrated with the switching mechanism in a simple compact unit.

In practice, the system may be entirely automated so that image correction takes place without human intervention. To this end, the motor of the rotor assembly is included in a servo loop which is coupled to the TV system. In the TV monitor, a cursor is electronically generated, the position of which is settable to identify the erect state of an image. The actual state of the image of the site viewed through the endoscope is then compared with the cursor to provide an error signal whose phase and magnitude is indicative of the deviation of the actual image from the erect state. This error signal is applied to the motor to cause it to correct for the image displacement.

The Primary Assembly

Referring now to FIG. 2, it will be seen that image-erecting barrel 13 is telescoped within the sleeve 34 of primary assembly 14. The inside diameter of this sleeve is somewhat greater than the outside diameter of the barrel so that the barrel is coaxially disposed therein, and the length of the sleeve is somewhat shorter than that of the barrel, so that the barrel projects from either end of the sleeve.

The opposing ends 34A and 34B of the sleeve are externally threaded to receive internally-threaded flanged rings 35A and 35B which when tightened on the sleeve ends act to compress elastomeric O-rings. These O-rings fit into the respective edges of the sleeve, which edges are chamfered so that the internal diameter of each edge is progressively reduced. The outer surface of the flanged compression rings is knurled to facilitate tightening.

Hence, as shown in FIG. 3, when compression ring 35B is tightened on sleeve end 34B, the flange of the compression ring engages and compresses O-ring 36B to flatten and elongate the ring, causing the ring to clamp onto the surface of the barrel 34. This clamping action serves to center the barrel on the longitudinal axis of the sleeve so that the barrel and sleeve are concentric. It will be appreciated that this arrangement makes it possible to quickly attach the primary assembly to the barrel of an articulated arm, or to withdraw the barrel from the assembly.

Sleeve 34 is concentrically supported by ball-bearings 37A and 37B within an outer cylindrical casing 38. Attached to the periphery of sleeve 34 is a ring gear 39, and mounted on casing 38 is a bi-directional dc motor 40 whose rotating shaft is coupled through a gear box 41 to a drive gear 42 that engages ring gear 39. The motor and gears are housed within a shroud 43 which is mounted on bracket 33.

Thus when the motor is energized, the resultant rotation of drive gear 42 is in a direction that depends on the polarity of the applied power, and it causes sleeve 34 and barrel 13 clamped therein to rotate. The gear ratio is such as to produce a relatively slow barrel rotation so that the operator, when he stops the motor, can do so at the exact point of image erection without overshoot.

The Power Supply and Switching Mechanism

As shown in FIG. 1, bi-directional dc motor 40 is connected to the movable poles of a double-throw, double-pole electrical switch 31 which is operated by foot pedal 32. Switch 31 is provided with a pair of right throw fixed contacts $R_1$ and $R_2$, right contact $R_1$ being connected to the positive output terminal of a bridge rectifier BR and right contact $R_2$ being connected to the negative output terminal.

Switch 31 is also provided with a pair of left throw fixed contacts $L_1$ and $L_2$; contact $L_1$ being connected to the negative terminal of the rectifier output and contact $L_2$ to the positive terminal, this being the reverse of the right throw contacts.

The input diagonals of the rectifier bridge BR are connected to the secondary of a transformer 44 whose primary is connected by a cable 45 to the ac power line by plug 46. The output diagonals are shunted by a filter capacitor 47. Connected between the negative and positive terminals through an on-off switch 48 is a load resistor 49.

At the neutral or center position of the foot switch 31, no power is applied. When the pedal 32 operatively coupled to the movable poles of the switch is rocked by the foot of the operator to the right, this causes the respective poles to engage right throw contacts $R_1$ and $R_2$, thereby energizing the motor to cause the barrel to turn clockwise. When the pedal is rocked to the left, the poles engage left throw contacts $L_1$ and $L_2$, causing the motor to turn the barrel in the counterclockwise direction.

Switch 48 acts as a speed selector; and when this switch is in its "off" position, the motor operates at relatively high speed; and when it is in the "on" position, the load resistor 49 is shunted across the rectifier output to provide low speed operation.

In practice, power may be supplied by a suitable battery, thereby obviating the need for an ac power cable and the possible hazards of such a cable in an operating room environment.

While there has been shown and described a preferred embodiment of an image-erecting barrel rotator for articulated optical arm in accordance with the invention, it will be appreciated that many changes and modifications may be made therein without, however, departing from the essential spirit thereof. Thus the motorized drive for the sleeve of the primary assembly may include a manually-operated knob, making it possible to turn the sleeve should the motor or its associated electrical controls become disabled in the course of a procedure. Also, instead of a reversible dc motor arrangement, a reversible ac motor arrangement may be provided.

I claim:

1. In combination, an articulated optical arm adapted to optically link to a viewing station the eyepiece of an endoscopic telescope which views an internal region, said arm including a series of sections mechanically interhinged and optically intercoupled by joints, a rotatable image-erecting barrel and a terminal eyepiece, the last section in the series being optically coupled through said rotatable image-erecting barrel to said terminal eyepiece, said arm being adjustable by an operator so that the endoscope may be extended, retracted or otherwise adjusted with respect to the internal region whereby any aspect of the internal region may be clearly viewed at the viewing station, the image transmitted through the arm undergoing circumferential displacement about the optical axis in a direction and to a degree that depends on this adjustment, and a barrel rotator comprising:

A. a primary assembly provided with a sleeve which telescopically receives and clamps onto said barrel and including a bi-directional motor operatively coupled to said sleeve to rotate the barrel either in the clockwise or counterclockwise direction, depending on the polarity of power supplied thereto; and B. a remote control station connected to the primary assembly and including selective means to supply power to the motor in a polarity and for a period effecting turning of the barrel in a direction and to an extent causing erection of the image presented through said terminal eyepiece.

2. The combination as set forth in claim 1, wherein said telescope is provided with an adapter to which a fiber optic cable is coupled to conduct light to illuminate said internal region.

3. The combination as set forth in claim 1, wherein the first section of the arm is provided with an optical coupler which fits onto the telescope eyepiece.

4. The combination as set forth in claim 1, wherein said viewing station is provided with means to optically couple said terminal eyepiece to the video camera of a TV monitor.

5. The combination as set forth in claim 4, wherein said viewing station further includes means to optically couple said terminal eyepiece to an auxiliary eyepiece.

6. The combination as set forth in claim 1, wherein said sleeve is provided at its edges at either end with an O-ring which is compressed by a flanged ring that is screwed onto the sleeve end to compress and flatten out the O-ring so that it engages the barrel to effect clamping thereof.

7. The combination as set forth in claim 1, further including a cylindrical casing concentric with the sleeve, said sleeve being supported by ball bearing within the casing, the motor being mounted on the casing.

8. The combination as set forth in claim 7, wherein said sleeve has a ring gear attached to its periphery, which is engaged by a drive gear operatively coupled to the motor.

9. The combination as set forth in claim 1, further including a foot pedal operatively coupled to said selective means whereby the operator, after adjusting said arm with his hands, may then re-erect said image by use of his foot on the pedal.

* * * * *